United States Patent [19]

Marinak et al.

[11] Patent Number: 4,507,486

[45] Date of Patent: Mar. 26, 1985

[54] PRODUCTION OF POLYCHLORINATED PYRIDINE MIXTURES BY LIQUID PHASE CHLORINATION OF 3,5-LUTIDINE OR 3,5-LUTIDINE HYDROCHLORIDE

[75] Inventors: Michael J. Marinak, Kelso; John L. Simonson, Longview, both of Wash.

[73] Assignee: Kalama Chemical, Inc., Kalama, Wash.

[21] Appl. No.: 486,377

[22] Filed: Apr. 19, 1983

[51] Int. Cl.$^3$ .......................................... C07D 213/61
[52] U.S. Cl. ................................................. 546/345
[58] Field of Search ........................................ 546/345

[56] References Cited

U.S. PATENT DOCUMENTS

| | | | |
|---|---|---|---|
| 3,420,833 | 1/1969 | Taplin | 546/345 |
| 3,573,315 | 3/1971 | Handele et al. | 546/345 |
| 3,732,230 | 5/1973 | Brewer et al. | 546/345 |
| 4,184,041 | 1/1980 | Nishiyama | 546/345 |
| 4,256,894 | 3/1981 | Dietsche et al. | 546/345 |

OTHER PUBLICATIONS

Werner et al., Chemical Abstracts, 97:92160f (1982).

*Primary Examiner*—Henry R. Jiles
*Assistant Examiner*—Robert C. Whittenbaugh
*Attorney, Agent, or Firm*—Graybeal & Cullom

[57] ABSTRACT

Preparation of high yields of mixtures rich in polychlorinated pyridines by maintaining a chlorine to 3,5-lutidine weight ratio of greater than about 7:1 when reacting chlorine and 3,5-lutidine or 3,5-lutidine hydrochloride non-catalytically in the liquid phase at temperatures in excess of about 150° C., the reactants being contained in a well mixed diluent producing 2 moles or less of hydrogen chlorine per mole of diluent by reaction with the chlorine in the indicated temperature range. Reaction in a primary reactor is followed by selective further chlorination to obtain desired final products useful as intermediates in the formation of herbicides and the like.

23 Claims, 1 Drawing Figure

PRODUCTION OF POLYCHLORINATED PYRIDINE MIXTURES BY LIQUID PHASE CHLORINATION OF 3,5-LUTIDINE OR 3,5-LUTIDINE HYDROCHLORIDE

BACKGROUND OF THE INVENTION

1. Field of the Invention

The present invention relates to preparation of polychlorinated pyridine mixtures by direct liquid phase chlorination of 3,5-lutidine or 3,5-lutidine hydrochloride. Typical of the products produced are 2,3,5,6-tetrachloropyridine; 5,6-dichloro- and 2,5,6-trichloro-3-trichloromethyl pyridine; 3,5-bis(trichloromethyl)pyridine; and 6-chloro- and 2,6-dichloro-3,5-bis(trichloromethyl)pyridine. These products have utility, for example, as intermediates for herbicides and insecticides. A further aspect of the present invention relates to further chlorination of mixtures rich in 3,5-bis(trichloromethyl) and 6-chloro-3,5-bis(trichloromethyl)-pyridine to form 5,6-dichloro-3-trichloromethyl pyridine and/or 2,3,5,6-tetrachloro pyridine, and the further chlorination of mixtures rich in 6-chloro-3,5-bis(trichloromethyl)pyridine and 2,6-dichloro-3,5-bis(trichloromethyl) pyridine to form 2,5,6-trichloro-3-trichloromethyl pyridine.

2. Description of the Prior Art

The utility of 2,3,5,6-tetrachloropyridine as an intermediate to insecticidal compositions is set forth in Dietsche et al U.S. Pat. No. 4,256,894.

Brewer et al U.S. Pat. No. 3,732,230 discloses liquid phase chlorination of 3,5-lutidine at 100° C. and 120° C. with greater than 30 psig of HCl partial pressure to yield unspecified polychlorinated lutidines.

Nishiyama U.S. Pat. No. 4,184,041 describes the utility of 5,6-dichloro-3-trichloromethyl pyridine in the production of herbicidal compositions.

SUMMARY OF THE INVENTION

It has been discovered that high yields of mixtures rich in chlorinated picolines/pyridines may be achieved by non-catalytically chlorinating 3,5-lutidine or 3,5-lutidine hydrochloride in a diluent in the liquid phase at temperatures of at least about 150° C. while maintaining strong agitation and a feed ratio of chlorine to 3,5-lutidine of at least about 7:1 by weight while feeding the chlorine and 3,5-lutidine or 3,5-lutidine hydrochloride to the reaction mass in a primary reactor. The 3,5-lutidine can be dissolved in carbon tetrachloride or fed full strength into the reactor. It is desirable to have a supply of carbon tetrachloride available for flushing the feed line in the event of a shutdown because stagnant 3,5-lutidine would otherwise tend to degrade in the feed line. If 3,5-lutidine hydrochloride is the desired feed form, it is fed directly through a sparger into the bottom of the primary reactor. After the 3,5-lutidine or 3,5-lutidine hydrochloride has been partially chlorinated in the primary reactor, the polychloro picoline is subjected to further chlorination in one or more reactors for such times and temperatures as appropriate to maximize the yield of the desired end product or products.

The percent of volatiles realized by liquid phase chlorination according to the present invention is dependent upon on the diluent composition, the extent of mixing the reactants and diluent, the 3,5-lutidine feed rate to reaction mass volume, the weight ratio of chlorine-to-3,5-lutidine being fed, and the chlorine partial pressure, which influences chlorine solubility. The composition of the diluent media in which the reaction proceeds is important in practice of this invention, to secure good yields of the desired volatile chlorinated pyridines. Its function in this invention is quite different from the initiator charge described in Taplin U.S. Pat. No. 3,424,754, which deals with alpha-picoline liquid phase chlorination. In U.S. Pat. No. 3,424,754, the initiator charge has the function of evolving HCl when contacted with chlorine at the reaction temperature in order to react with alpha-picoline to form picoline hydrochloride. In the present invention the diluent's function is to be reactively less competitive for the chlorine dissolved in it and to help remove the heat of reaction evolved by the chlorination of the 3,5-lutidine.

Examples of some compounds usable as diluents in practice of the present invention, in that they generate 2 moles or less of HCl per mole of compound when contacted with chlorine under the reaction conditions of the present invention, are: 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, 3,5-bis(trichloromethyl)pyridine, 6-chloro- and 2,6-dichloro-3,5-bis(trichloromethyl)pyridine, and 2,3,6-trichloro-, 2,3,5,6-tetrachloro-, and 2,3,4,5,6-pentachloro pyridine, and mixtures thereof. This list is not meant to be exhaustive of all possible diluent constituents but is illustrative of compounds useful for the purpose. The diluent may be the chlorinated pyridine/lutidine products from a previous reaction which meet the above criteria and is high in volatiles content.

In practice of the present invention, an excess of chlorine is fed relative to that needed for the 3,5-lutidine or 3,5-lutidine hydrochloride chlorination, which excess provides additional agitation and hence better mixing, and also a higher chlorine partial pressure which increases the chlorine solubility in the reaction media. A chlorine-to-3,5-lutidine weight ratio of at least about 7:1 is needed. As the temperature increases in excess of 200° C., the weight ratio of chlorine to 3,5-lutidine fed needs to be higher in order to achieve the high yields of the desired volatile chloro-pyridines. This is necessary because chlorine reacts more rapidly with the 3,5-lutidine or 3,5-lutidine hydrochloride as the temperature increases and therefore the chlorine dissolved in the reaction medium must be more rapidly replaced. This is accomplished by increasing the rate of chlorine addition relative to the 3,5-lutidine flow rate which increases the chlorine partial pressure and hence its mole fraction in the liquid reaction medium. Gas solubilities tend to decrease with rising temperature, but an increase in system pressure also increases the chlorine solubility.

The 3,5-lutidine or 3,5-lutidine hydrochloride feed is to be controlled relative to the reaction volume so no more than about 10% by volume of light phase accumulates relative to the chlorinated pyridine phase at temperatures in excess of about 150° C. Potential decomposition products can result above this temperature in the absence of cooling and excess chlorine. Since 3,5-lutidine hydrochloride and the diluent are somewhat immiscible and of different densities, good mixing is necessary in order to achieve dispersion of chlorine and 3,5-lutidine or 3,5-lutidine hydrochloride into the diluent.

Controlling these variables results in the high yields of volatile polychlorinated pyridines in the liquid phase at temperatures in excess of 150° C.

Care must be taken to ensure metallic impurities such as iron, copper, aluminum and other Lewis Acid type metals are excluded from the reaction mass, as they will cause different reactions in the chlorination that may not be desirable.

DESCRIPTION OF THE PREFERRED EMBODIMENTS

Example 1

Figure 1:
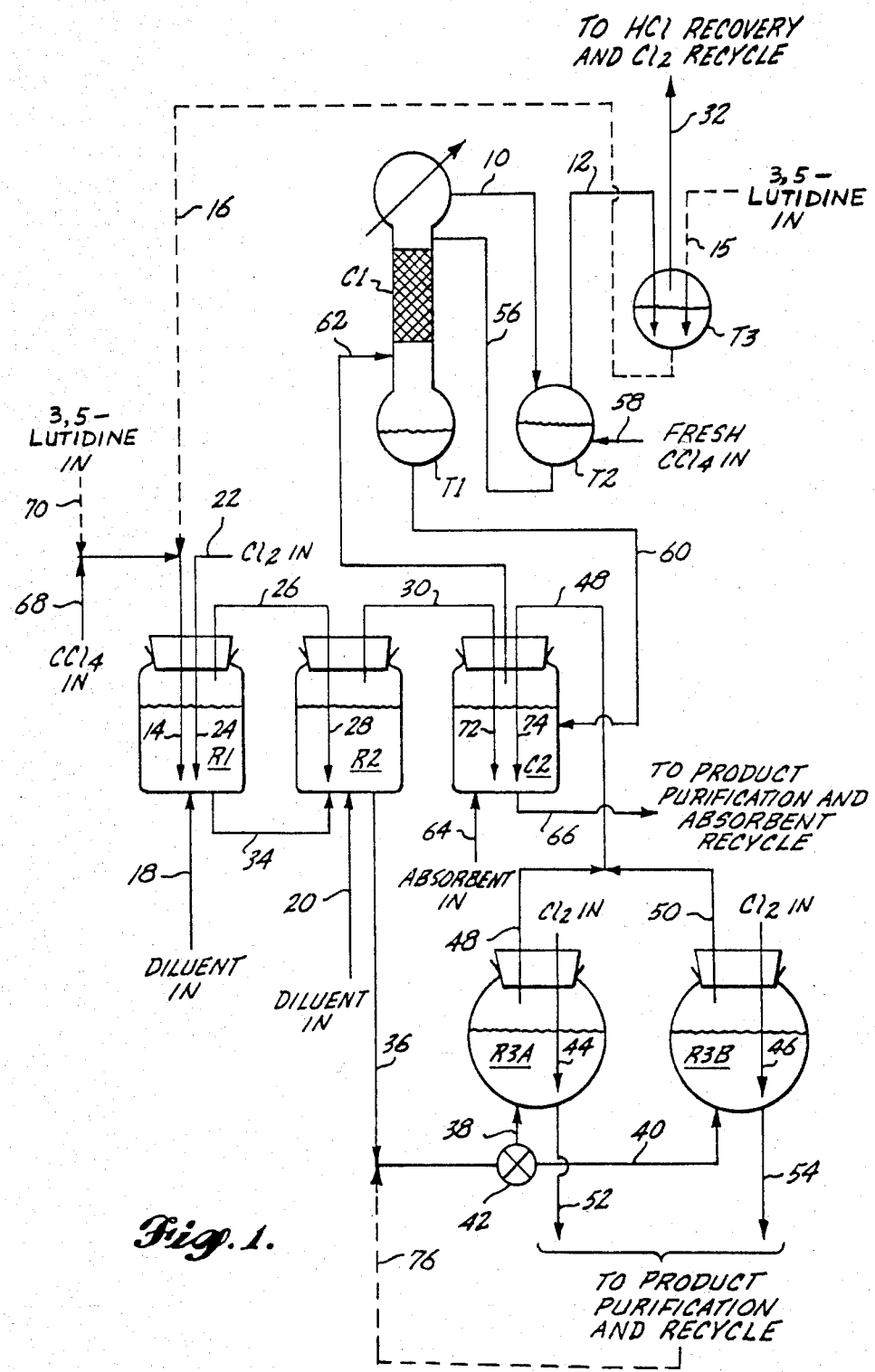
FIG. 1 is a schematic diagram of a reaction system for practicing the process of the present invention on a continuous batch basis.

FIG. 1 schematically illustrates a continuous batch type reaction system for producing mixtures rich in polychlorinated pyridines according to the present invention. Primary reactor R1, secondary reactor R2, and absorber C2 are suitably glass of cylindrical configuration, electrically heated and each about 1 liter in volume, and with an inside diameter of 4 inches and an inside height of 7 inches. Finishing reactors R3A and R3B are glass, spherical, electrically heated and about 1 liter in volume. Water cooled scrubber column C1 is suitably of cylindrical design, 1½ inches in diameter, containing as packing some 18 inches of ¼ inch glass rings.

Scrubber column C1 includes a holding tank or reservoir T1 and the overhead vapor from column C1 is delivered through vent line 10 to disengaging tank T2 in which the carbon tetrachloride collects, with the chlorine and hydrogen chloride evolving from column C1 being delivered by vent line 12 and sparged into hydrochlorination tank T3. For startup, 3,5-lutidine hydrochloride, suitably previously prepared conventionally as by sparging anhydrous HCl into a pool of 3,5-lutidine maintained between 80° C. and 100° C. until saturated with HCl, is charged to hydrochlorination tank T3 and 3,5-lutidine hydrochloride is withdrawn from tank T3 and delivered to bottom discharging sparger 14 in reactor R1 through line 16. An alternate startup mode involves feeding 3,5-lutidine dissolved in carbon tetrachloride through lines 68 and 70 thence into line 14, generating hydrogen chloride which is vented to hydrochlorination tank T3. For startup, also, primary reactor R1 was charged through charge line 18 with 1095 grams of diluent, consisting of chlorinated pyridine from a previous reaction (suitably comprising about 22.0% 2-trichloromethyl pyridine, 63.0% 6-chloro-, 7.6% 5,6-dichloro-, 2.2% 3,6-dichloro-, and 1.2% 3,5,6-trichloro-2-trichloromethyl pyridine by weight). 533 grams of like diluent material was also charged to secondary reactor R2 through charge line 20. 225 grams of a suitable absorbent was charged through charge line 64 to absorber C2, the composition of the absorbent selected for this example being the same as in R1 and R2. The absorbent charged to C2 needs to have a melting point of less than 80° C. and substantial solubility with carbon tetrachloride. Its purpose is to absorb higher melting chlorinated pyridines, e.g. those with melting points greater than 90° C., namely, 2,3,5,6-tetra- and 2,3,4,5,6-pentachloro pyridine. If these higher melting point chloropyridines were allowed to enter the scrubber column C1 in substantial quantity, they would tend to plug the column packing. The refluxing carbon tetrachloride in scrubber column C1 tends to concentrate in the entrained chloropyridine that enter it in the bottom tank T1 thereof, and keep the overhead vapors substantially free of chlorinated pyridines which would otherwise plug the vapor outlet 10. Some typical examples which meet the criteria of suitable absorbent materials are 6-chloro-5,6-dichloro-, 3,6-dichloro-, 3,5-dichloro-2-trichloromethyl pyridine, and mixtures thereof.

The operational startup sequence is that of introducing the diluent to the primary and secondary reactors, then initiating chlorine flow, then heating the reactors to desired reaction temperature, then initiating the 3,5-lutidine or 3,5-lutidine hydrochloride flow. By this procedure the 3,5-lutidine or 3,5-lutidine hydrochloride only sees excess chlorine in the reactors and degradation thereof to nonvolatiles is avoided. Once reactors R1 and R2 were charged, external heat was applied and the temperature of primary reactor R-1 thereof was maintained at 230° C., with secondary reactor R2 being maintained at 230° C. and absorber C2 maintained at 140° C. Chlorine gas from a suitable pressurized source was delivered to the reactor R1 through feed line 24 and bottom placed sparger 24 at a flow rate of 380 grams per hour. A flow of 3,5-lutidine dissolved in carbon tetrachloride at a volume ratio of 1:2 was sparged into reactor R1 through bottom placed sparger 14, the discharge stream of which is closely adjacent (with about ½ inch spacing) to the discharge stream of chlorine sparger 24, was maintained at a rate equivalent to 29.6 grams 3,5-lutidine per hour, amounting to a chlorine to lutidine feed ratio of about 12.8:1.

The hydrogen chloride generated from the reaction along with excess chlorine is vented from reactor R1 through vent line 26 and sparged into the charge in secondary reactor R2 through bottom discharging sparger 28, the overhead vapor including hydrogen chloride and excess chlorine being vented from reactor R2 and delivered through line 30 to absorber C2, thence through line 62 to scrubbing column C1, thence through line 10 and line 12 to hydrochlorinating tank T3, the vapor flow from which passes through line 32 to hydrogen chloride and chlorine gas recovery means known per se, for recycling of the chlorine gas to the process and recovery of the hydrogen chloride, as desired. Once hydrogen chloride gas is being generated and is passing through the system to hydrochlorination tank T3, the 3,5-lutidine feed into tank T3 through line 15 can be started if that is the desired feed mode.

Secondary reactor R2 is only partially charged with diluent at startup. This is for the reason that, as the volume of the reaction mass in reactor R1 increases in the course of the reaction, a portion of the reaction mass is moved from reactor R1 to reactor R2 (by volatilization and entrainment) through line 26 and through discharge line 34 for further chlorination in reactor R2. The temperature in secondary reactor R-2 influences the degree of continued chlorination. In this example a temperature of 230° C. was selected in order to continue the chlorination at a high rate of reaction. A higher temperature in secondary reactor R3, such as a temperature greater than 260° C., would continue the chlorination process at a higher rate than occurs at 230° C. In this example, reactors R3A and R3B were chosen to take the reaction to the desired degree of chlorination by operating at 260° C. for 2 hours.

When the liquid volume in secondary reactor R2 increases to the point where the reactor R2 is filled to its operating level, further increase in liquid volume is taken care of by progressively discharging the excess through line 36 to either finishing reactor R3A through line 38, or to finishing reactor R3B through line 40, depending on the setting of valve 42.

Chlorination to process end point is completed in either reactor R3A or reactor R3B by continued introduction of chlorine gas through bottom discharging sparger 44 or 46, with continued heating of the reactors R3A or R3B to a desired temperature for a desired time to yield the desired product distribution, e.g. a temperature of 260° C. and a time of 2 hours, in this selected example. Chlorine and hydrochloride vapor takeoff from reactors R3A and R3B is delivered through vent lines 48, 50 to absorber C2 through sparge line 74, thence to scrubber column C1.

Chlorinated reaction product is withdrawn from the reactors R3A and R3B through respective discharge lines 52, 54, with the product going to product purification means known per se, such as a vacuum fractional distillation column. Liquid discharge from holding tank T2 is delivered to scrubber column C1 through line 56 to return carbon tetrachloride to the column C1, with makeup of carbon tetrachloride from an appropriate supply if necessary, as indicated at 58. The liquid phase fraction collecting in bottom tank T1 of the scrubber column C1 is returned to absorber C2, as indicated at line 60.

Finishing reactors R3A and R3B can be smaller or larger than reactors R1 and R2, depending on the desired residence time to complete the chlorination reaction. For example, with a reaction temperature of 230° C. and a residence time of 9 hours in the primary reactor R1 and a reactor temperature of 230° C. and a residence time of 9 hours in the secondary reactor R2, the time required to complete the reaction in reactor R3A or in reactor R3B is about 2 hours at 260° C. temperature. The controlling factor determining reaction time in reactor R3A or reactor R3B is the maximum concentration of the desired product. The desired principal product is 5,6 dichloro-3-trichloromethyl pyridine, and a chlorination time of 2 hours to 260° C. was chosen. If the principal desired product is 2,3,5,6-tetrachloro pyridine, more time would be required in R3A or R3B. In this first example it has been assumed that a mixture of end product compounds, with each compound present in substantial proportion, was desired, and to this end the composition of the end product obtained in R3A and R3B comprised 18.0% 2,3,5,6-tetrachloro pyridine, 24.8% 5,6-dichloro-3-trichloromethyl pyridine, and 29.2% 2,5,6-trichloro-3-trichloromethyl pyridine, 19.6% 6-chloro-3,5-bis(trichloromethyl)pyridine, and 8.3% 2,6-dichloro-3,5-bis(trichloromethyl)pyridine, by weight. Further, product purification and recycle to R3A or R3B for further chlorination, as indicated at 76, can convert the 6-chloro-3,5-bis(trichloromethyl)pyridine to 5,6-dichloro-3-trichloromethyl pyridine and the 2,6-dichloro-3,5-bis(trichloromethyl)pyridine to 2,3,5,6-tetrachloro pyridine.

Excess chlorine, hydrogen chloride and some volatile corrosive chloro-pyridine hydrochlorides and entrained chlorinated pyridines, some of which have melting points in excess of 100° C., are transferred to secondary reactor R2 from primary reactor R1 by heated vent line 26 and bottom discharging sparger 28, with the volatile hydrochlorides being absorbed and reacted further in secondary reactor R2. These hydrochlorides are very corrosive and tend to form solids on condenser surfaces that are in the 30° C. to 100° C. temperature range, the operating temperature range of scrubber column C1 and, along with the high melting chloropyridines, would there cause a plugging problem in column C1 if passed directly from primary reactor R1 to the scrubber column C1. Their absorption and further reaction in secondary reactor R2 help eliminate such plugging problems and absorber C2 completely eliminates the high melting chloropyridines in the vent line 62 to column C1. The excess chlorine, hydrogen chloride and entrained products passing to column C1 through absorber C2 vent line 62 are there scrubbed with carbon tetrachloride discharged to column C1 through line 56. The entrained chlorinated pyridine products buildup in tank T1 and the liquid level therein is controlled by recycling the excess liquid back to absorber C2 through discharge line 60. When the level in absorber C2 reaches the operating level, processing of the excess material is begun through line 66 for removal of the high melting chloropyridine reaction products from the absorber material. These chlorinated pyridine products are removed from the absorbent material by vacuum distillation. Process absorbent is then recycled back to C2 through line 64.

As will be apparent, finishing reactors R3A and R3B are operated in a batch manner, permitting one to be on line while the other is having the chlorinated product removed or is being filled from secondary reactor R2. Analysis of the reaction mass is the on line reactor R3A or R3B for maximum concentration of the desired chloropyridine(s) indicates when the reaction is finished. When this occurs the contents of the on line reactor R3A or R3B are pumped through the respective discharge lines 52 or 54 to the purification section of the system, suitably involving a conventional vacuum distillation system.

The residence time in each reactor R1, R2 and R3A or R3B typically varies from about .1 to about 40 hours, and the total cycle time in the reactors is about 10 to 120 hours. From the previously described feed and reaction conditions set forth in Example 1, 84 grams per hour of product was obtained that contained about 24.8% 5,6-dichloro-, and 29.2% 2,5,6-trichloro-3-trichloromethyl pyridine, and 19.6% 2-chloro- and 8.3% 2,6-dichloro-3,5-trichloromethyl pyridine, by weight. In addition, 18.0% 2,3,5,6-tetrachloro pyridine was present. The volatiles content of the reaction mass was greater than 99%. In this example, also, the total residence time was about 20 hours. In practice of the invention appropriate variation in residence time is determinable on a predictable basis, taking into consideration the product composition desired, and the reactor pressure and reactor temperature. In addition, the quantity of diluent recycled to the reactors may also be varied to vary the residence time. In any event, as earlier indicated, the feed rate of 3,5-lutidine or 3,5-lutidine hydrochloride relative to the reaction volume is to be controlled so that no greater than about 10% by volume of lighter phase (undiluted lutidine hydrochloride) exists in the reaction mass.

The gases in vent line 32 from hydrochlorination tank T3 are predominantly excess chlorine and hydrogen chloride, which stream can be separated or purified by a number of conventional techniques such as absorption of the hydrogen chloride in water, or drying the chlorine and compressing the chlorine gas for recycle, or fractional distillation.

The analyses of the reaction products obtained in Example 1 is given in the following Table One.

TABLE ONE

| Compound | Example 1 |
|---|---|
| 2,3,5,6-tetrachloropyridine | 18.0% |
| 2,3-dichloro-5-(trichloromethyl)pyridine | 28.8 |
| 3-chloro-2,6-bis(trichloromethyl)pyridine | 19.6 |
| 2,3,6-trichloro-5-(trichloromethyl)pyridine | 29.2 |
| 3,5-bis(trichloromethyl)-2,6-dichloropyridine | 8.3 |

Examples 2 through 6

Examples 2 through 6 serve to illustrate some of the process variables which can occur in practice of the present invention, and for such purpose were conducted as simplified batch processes. A chlorination reactor comprising a 1000 ml spherical glass reactor (except in Example 2 where a 250 ml spherical glass reactor was employed), heated by an electric heating mantle, was equipped with two sparge tubes and a line which was vented through a 5000 ml glass knockout pot to a caustic scrubber. The spargers were bottom placed and closely spaced (2 centimeters apart) and the respective feed lines to the spargers were fed through rotometers and flow controlled through respective needle valves, one being supplied from the source of chlorine gas, and the other supplied from a source of 3,5-lutidine (Examples 2 through 5) or 3,5-lutidine hydrochloride (Example 6). In each run the procedure followed was the same except for the variables investigated, namely diluent composition, temperature, chlorine-to-3,5-lutidine feed ratio, residence time, and lutidine flow rate relative to reaction mass volume. In Example 2, which is illustrative, the reactor was charged with 50 grams of diluent, the composition of which is given in the following Table Two, and chlorine feed was initiated through the chlorine sparger at the rate of 70 grams per hour and the charge heated to a temperature of 150° C. 3,5-lutidine was then sparged into the reactor at the rate of about 3.3 grams per hour for a period of 5 hours. The weight ratio of chlorine to the 3,5-lutidine being fed during the reaction was about 21:1. Chlorine feed was continued at the rate of 70 grams per hour for 9 more hours at a temperature of 200° C., 8 hours at 220° C., and 2 hours at 260° C. after the lutidine feed was discontinued. The reaction process parameters are tabulated in the following Table Three. The gross weight of the resulting reaction product was 104 grams, indicating a net production of 54 grams of product. The product was a clear tractable fluid, with a volatiles proportion of greater than 98%, as measured by internal standard gas chromatography. The constituency of the product was as tabulated in Table Four.

As indicated, additional runs, designated Examples 3, 4, 5 and 6 involved the diluents set forth in Table Two, the parameters set forth in Table Three and produced reaction products comprising the compounds set forth in Table Four.

TABLE TWO

| Compound | DILUENT COMPOSITION | | | | |
|---|---|---|---|---|---|
| | Ex. 2 | Ex. 3 | Ex. 4 | Ex. 5 | Ex. 6 |
| 2-(trichloromethyl)pyridine | 5.3% | | | | |
| 2,6-dichloropyridine | | | | 3.6% | 1.2% |
| 2,3,6-trichloropyridine | 1.2 | | | 8.0 | |
| 2-chloro-6-(trichloromethyl)pyridine | 77.8 | 21.5% | | | 50.7 |
| 2,6-dichloro-3-(trichloromethyl)pyridine | 6.2 | | | | 11.3 |
| 2-chloro-3-(trichloromethyl)pyridine | 2.7 | | | | |
| 2,3-dichloro-6-(trichloromethyl)pyridine | 1.9 | 67.7 | 94.4% | | |
| 3-chloro-2-(trichloromethyl)pyridine | | | | 8.1 | 4.2 |
| 2,5-dichloro-6-(trichloromethyl)pyridine | | | | | 52.5 |
| 2,5-dichloro-3-(trichloromethyl)pyridine | | | | | 10.5 |
| 3-chloro-6-(trichloromethyl)pyridine | | | | | 5.9 |

TABLE TWO-continued

DILUENT COMPOSITION

| Compound | Ex. 2 | Ex. 3 | Ex. 4 | Ex. 5 | Ex. 6 |
|---|---|---|---|---|---|
| 2-Cl, 3-CCl3, 5-Cl pyridine | | | | | 1.9 |
| 2-Cl, 3-Cl, 5-CCl3 pyridine (with Cl) | | | | | 4.5 |
| 2-Cl, 3-Cl, 5-CCl3, 6-Cl pyridine | | | | | 7.5 |
| 2-CCl3, 5-CCl3 pyridine | | | | | 18.1 |
| 2-CCl3, 3-Cl, 5-CCl3 pyridine | | | | | 18.6 |

TABLE THREE

|  | Ex 2 | Ex 3 | Ex 4 | Ex 5 | Ex 6 |
|---|---|---|---|---|---|
| Initial Reactor Temp | 150° C. | 210° C. | 225° C. | 240° C. | 190° C. |
| Diluent charge | 50 gms | 480 gms | 451 gms | 589 gms | 488 gms |
| Feed Form | 3,5-lutidine | 3,5-lutidine/CCl4 | 3,5-lutidine/CCl4 | 3,5-lutidine/CCl4 | 3,5-lutidine HCl |
| Cl2 Flow Rate | 70 gms/hr | 380 gms/hr | 380 gms/hr | 380 gms/hr | 440 gms/hr |
| 3,5-lutidinee | 3.3 gms/hr | 11.2 gms/hr | 39.2 gms/hr | 27 gms/hr | 17.9 gms/hr |
| Cl2/3,5-lutidine ratio (by weight) | 13.5:1 | 34.1 | 9.2:1 | 14:1 | 24.6:1 |
| Reaction Time with both Cl2 and 3,5-lutidine feeds | 5 hrs | 5 hrs | 2 hrs | 5 hrs | 2½ hrs |
| Additional reaction time and temp with Cl2 feed only | 9 hrs @ 210° C. + 8 hrs @ 220° C. + 2 hrs @ 260° C. | 2½ hrs @ 260° C. | 2 hrs @ 260° C. | 6 hrs @ 260° C. | 2 hrs @ 260° C. |
| Amt of product produced | 54 gms | 160 gms | 224 gms | 388 gms | 132 gms |
| Volatility of produced product | <98% | 99% | 99% | 99% | <98% |

TABLE FOUR

| Compound | Example 2 | Example 3 | Example 4 | Example 5 | Example 6 |
|---|---|---|---|---|---|
| 2,3,5,6-tetrachloropyridine | 3.5% | 13.2% | 6.1% | 17.5% | 5.0% |
| pentachloropyridine | | 37.0 | | | |
| 2,3-dichloro-5-(trichloromethyl)pyridine | 3.5 | 25.2 | 23.1 | 27.7 | 27.2 |
| 2,3,6-trichloro-5-(trichloromethyl)pyridine | 27.2 | 26.4 | 19.0 | 34.8 | 17.7 |
| 3-chloro-2,5-bis(trichloromethyl)pyridine | 3.3 | 26.8 | 39.7 | 16.4 | 39.9 |

TABLE FOUR-continued

| Compound | Example 2 | Example 3 | Example 4 | Example 5 | Example 6 |
|---|---|---|---|---|---|
| Cl₃C-pyridine-CCl₃ with Cl,Cl | 3.0 | 12.2 | 12.0 | — | 10.1 |

The following Examples 7 through 11 are presented in order to explain the chemistry involved in the continued chlorination of the effluent product from reactor R2. In addition, various reaction temperatures were explored in order to determine the range of operability for these chlorination reactions.

Example 7

Seventy-five grams of a mixture containing 24.3% 3,5-bis(trichloromethyl)pyridine and 6.5% 6-chloro-3,5-bis(trichloromethyl)pyridine were chlorinated in the liquid phase for 1 hour at 280° C. Chlorine at a flowrate of 70 grams/hour was sparged into the 250 ml chlorinator. Table 5 gives the analysis of the mixture initially and after 1 hour of chlorination. The 3,5-bis(trichloromethyl)pyridine concentration went from 24.3% to 1.3%, while the 5,6-dichloro- and the 2,5,6-trichloro-3-trichloromethyl pyridine concentrations went from zero to 8.0% and zero to 5.1% respectively. The concentration of 6-chloro- and 2,6-dichloro-3,5-bis(trichloromethyl)pyridine increased from 6.5% to 20.4% and zero to 4.3%, respectively. This example illustrates that 3,5-bis(trichloromethyl)pyridine chlorinates in the liquid phase to two main chlorination products, namely, 5,6-dichloro-3-trichloromethyl pyridine and 6-chloro-3,5-bis(trichloromethyl)pyridine.

This illustrates the predominant reactions occurring in Example 7:

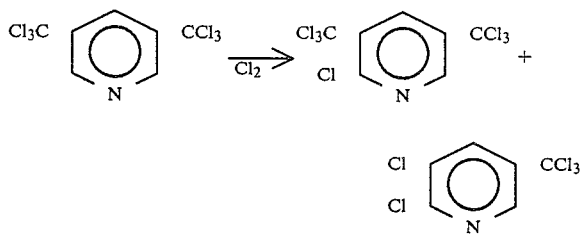

TABLE 5

| Compound | Initial | 1 hr @ 280° C. |
|---|---|---|
| Cl,Cl-pyridine-Cl,Cl | | 1.7% |
| Cl₃C-pyridine-CCl₃ | 24.3% | 1.3 |
| Cl,Cl-pyridine-CCl₃ | | 8.0 |
| Cl,Cl-pyridine-CCl₃ (with Cl) | | 5.1 |
| Cl₃C-pyridine-CCl₃ with Cl | 6.5 | 20.4 |
| Cl₃C-pyridine-CCl₃ with Cl,Cl | | 4.3 |

Example 8 shows that further chlorination of 6-chloro-3,5-bis(trichloromethyl)pyridine yields some 5,6-dichloro-3-trichloromethyl pyridine but predominantly 2,5,6-trichloro-3-trichloromethyl pyridine.

Example 8

Seventy-five grams of a chlorinated pyridine mixture containing 20.4% 6-chloro-3,5-bis(trichloromethyl)-pyridine were chlorinated with 70 grams/hr of chlorine for 1 hour at 280° C. The three main products of reaction were 5,6-dichloro- and 2,5,6-trichloro-3-trichloromethyl pyridine and 2,3,5,6-tetrachloropyridine. Table 6 lists the complete analysis.

This illustrates the predominant reactions occurring in Example 8:

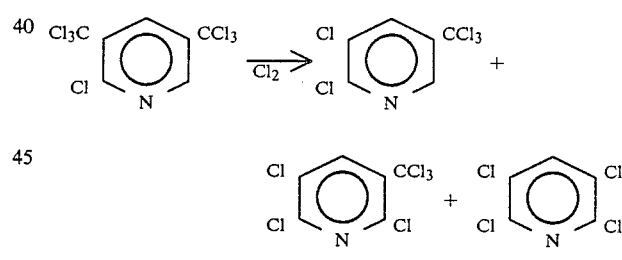

TABLE 6

| Compound | Initial | 1 hr @ 280° C. |
|---|---|---|
| Cl,Cl-pyridine-Cl,Cl | 1.7% | 8.1% |
| Cl₃C-pyridine-CCl₃ | 1.3 | — |
| Cl,Cl-pyridine-CCl₃ | 8.0 | 9.9 |

TABLE 6-continued

| Compound | Initial | 1 hr @ 280° C. |
|---|---|---|
| Cl, CCl3, Cl, Cl pyridine | 5.1 | 11.9 |
| Cl3C, CCl3, Cl pyridine | 20.4 | 6.9 |
| Cl3C, CCl3, Cl, Cl pyridine | 4.3 | 3.1 |

Example 9 illustrates the results of further chlorination of 5,6-dichloro- and 2,5,6-trichloro-3-trichloromethyl pyridine.

Example 9

970 grams of products rich in 5,6 dichloro- and 2,5,6-trichloro-3-trichloromethyl pyridine were charged to a chlorinator. 200 grams per hour of chlorine was sparged into the bottom of the chlorinator for 8 hours at a reaction temperature of 260° C. and for 3 hours at a reactor temperature of 230° C. The 5,6-dichloro-3-trichloromethyl pyridine content decreased from 10.6 mole percent to 4.3 mole percent, while 2,5,6-trichloro-3-trichloromethyl pyridine content decreased from 19.1 mole percent to 9.2 mole percent. The 2,3,5,6-tetrachloro pyridine content of the mass increased from 28.5 mole percent to 44.2 mole percent.

In summary:

| | Cl,CCl3,Cl pyridine →Cl2→ | Cl,CCl3,Cl,Cl pyridine →Cl2→ | Cl,Cl,Cl,Cl pyridine | total moles |
|---|---|---|---|---|
| Start | 10.6% | 19.1% | 28.5% | 58.2% |
| Finish | 4.3% | 9.2% | 44.2% | 57.7% |

The above reactions occur during the production of 2,3,5,6-tetrachloro pyridine from 5,6-dichloro-3-trichloromethyl pyridine via 2,5,6-trichloro-3-trichloromethyl pyridine.

Example 10

Seventy-five grams of a mixture rich in 3,5-bis(trichloromethyl)pyridine and 6-chloro-3,5-bis(trichloromethyl)pyridine were chlorinated at 70 grams/hr at 260° C. for seven hours. The initial analysis and final analysis listed in Table 7 shows the main reaction products to be 2,3,5,6-tetrachloropyridine, 5,6-dichloro- and 2,5,6-trichloro-3-trichloromethyl pyridine. This Example illustrates the overall net result of the chlorination reactions described in Examples 7, 8 and 9.

This illustrates the overall chemistry occurring in reactors R3A or R3B:

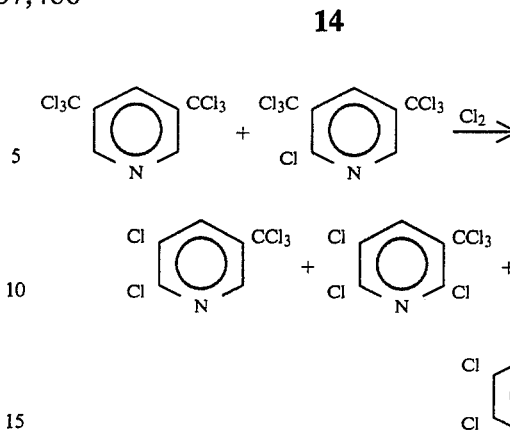

TABLE 7

| Compound | Initial | 7 hrs @ 260° C. |
|---|---|---|
| Cl,Cl,Cl,Cl pyridine | 0.7% | 24.0% |
| Cl,CCl3,Cl pyridine | 1.2 | 3.5 |
| Cl,CCl3,Cl,Cl pyridine | — | 7.9 |
| Cl3C,CCl3 pyridine | 17.0 | — |
| Cl3C,CCl3,Cl pyridine | 16.4 | — |
| Cl3C,CCl3,Cl,Cl pyridine | 1.3 | — |

Example 11

Seventy-five grams of a mixture containing 24.3% 3,5-bis(trichloromethyl pyridine and 6.5% 6-chloro-3,5-bis(trichloromethyl)pyridine were chlorinated with 70 grams per hour of chlorine at 190° C. for 8 hours. Analysis is listed in Table 8. The 5,6-dichloro-3-trichloromethyl pyridine concentration went from zero to 0.5% and the 2,6-dichloro-3,5-bis(trichloromethyl)pyridine went from zero to 0.7%. The 3,5-bis(trichloromethyl)pyridine went from 24.3% to 18.1% while the 6-chloro-3,5-bis(trichloromethyl)pyridine increased from 6.5% to 14.0%. Temperatures below 190° C. give unacceptably slow reaction rates to produce 5,6-dichloro-3-trichloromethyl pyridine and 2,3,5,6-tetrachloropyriidine.

TABLE 8

| Compound | Initial Concentration | 8 hrs @ 190° C. |
|---|---|---|
| 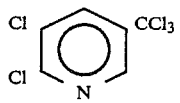 | — | 0.5% |
| 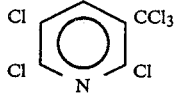 | — | — |
| 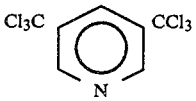 | 24.3% | 18.1 |
| 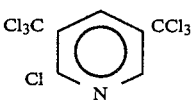 | 6.5 | 14.0 |
| 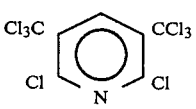 | — | 0.7 |

We have now discovered that from 150° C. up to higher liquid phase chlorination temperatures, e.g. 240° C., a whole series of useful reaction products is realized, and at temperatures of about 190° C. and above there is very little 2,3,4,5,6-pentachloropyridine formed. Typical compositions at 190° C. and higher reaction temperatures in the primary reactor involve about 20–30% 5,6-dichloro-3-trichloromethyl pyridine, 20–35% 2,5,6-trichloro-3-trichloromethyl pyridine, 16–40% 6-chloro-3,5-bis(trichloromethyl)pyridine by weight and smaller amounts on the order of 10% of the 2,6-dichloro-3,5-bis(trichloromethyl)pyridine. We have also discovered that these products can be further chlorinated, at predictable functions of time vs. temperature, to give other useful intermediates. For example, when subjected to further chlorination in liquid phase at high temperature, 5,6-dichloro-3-trichloromethyl pyridine goes to 2,5,6-trichloro-3-trichloromethyl pyridine. Similarly 6-chloro-3,5-bis(trichloromethyl)pyridine chlorinates to 2,5,6-trichloro-3-trichloromethyl pyridine and 5,6-dichloro-3-trichloromethyl pyridine. The process can be interrupted at this stage and these two main components, namely the 5,6-dichloro-3-trichloromethyl pyridine and the 6-chloro-3,5-bis(trichloromethyl)pyridine may be separated out, or, if chlorination is continued, the 5,6-dichloro-3-trichloromethyl pyridine goes to 2,5,6-trichloro-3-trichloromethyl pyridine and on still further chlorination to 2,3,5,6-tetrachloro pyridine, which has great utility as an intermediate in insecticidal compositions. The process can be selectively controlled to realize a very high yield of 2,3,5,6-tetrachloro pyridine, or the yield of 5,6-dichloro-3-trichloromethyl pyridine and 2,3,5,6-tetrachloropyridine, both of which have utility as intermediates for herbicides, can be maximized by not chlorinating as long. The foregoing Example 1 illustrates approximate maximal production of 5,6-dichloro-3-trichloromethyl pyridine and 2,3,5,6-tetrachloro pyridine.

In general, the primary reactor R1 is maintained at a temperature of at least 150°. Its maximum practical temperature for practice of the present invention is that temperature at which it can be safely operated in the liquid phase. Retention time in the primary reactor R1 should also be such that there is no unreacted 3,5-lutidine or 3,5-lutidine hydrochloride in vent line 26 or in the liquid passed to the secondary reactor R2 through line 34. In what is considered the best mode for practice of the invention (Example 1), the secondary reactor R2 is maintained at 230° C. Finishing reactors R3A and R3B are also run at a selected temperature, 260° C. in the case of Example 1, and a selected time, 2 hours in Example 1, to get a maximum composition of the desired products, e.g. in Example 1 to get 6-chloro-3,5-bis(trichloromethyl)chloromethyl pyridine and 5,6-dichloro-3-trichloromethyl pyridine and the derivatives that go to 2,3,5,6-tetrachloro pyridine on further chlorination. If the reaction objective is to make a product rich in 2,3,5,6-tetrachloro pyridine, secondary reactor R2 should be run very hot and the finishing reactors R3A and R3B also should be run very hot for a longer period of time, since these final products are "at the end of the line", from the point of view of progressive chlorination reaction.

The main criteria for the absorbent charge in absorber C2 is that it is non-reactive at the temperature at which the absorber operates (140° C.), is a compound or mixture of compounds having a melting point less than 80° C., and is mutually soluble in carbon tetrachloride, so that it doesn't plug up the scrubbing column C1, either through not melting or freezing or lack of solubilization. The absorber charge, being non-reactive, is basically a one time charge and recycled after removal of the absorbed product components, with only slight makeup from time to time. Functionally, the absorbent acts and is handled in much the same way as the carbon tetrachloride in the scrubbing column C1.

The chlorination process described in Taplin U.S. Pat. No. 3,424,754 relies on chlorine gas sparging into the liquid reaction mass to dissolve the chlorine in the reaction mass and to mix alpha-picoline hydrochloride with the initiator charge. According to Chemical Engineering Handbook, Perry, 3rd Edition, page 1215 (1950), agitation produced by the degree of gas sparging involved in the process of U.S. Pat. No. 3,424,754 (estimated to be about 1.5 cubic foot per square foot minute at 200° C.) is usually too mild to move immiscible liquids with appreciable density differences into good contact with each other. In reactions according to the present invention, it is a practical necessity to maintain the reaction mass well mixed so that there is good contact and quick dispersion of the 3,5-lutidine or 3,5-lutidine hydrochloride into the diluent at the desired reaction temperatures of greater than 150° C. because the polychlorinated pyridine diluent and the 3,5-lutidine hydrochloride are immiscible and have substantially different densities (about 1.6 and about 1.2 grams per cubic centimeter, respectively), and because 3,5-lutidine hydrochloride is unstable in this temperature range, i.e.

the salt tends to break down to its components, namely hydrogen chloride and 3,5-lutidine. If there is breakdown into the components, the hydrogen chloride is volatile and escapes through the vent system and 3,5-lutidine builds up in a lighter liquid phase.

Yields of volatile chlorinated pyridines in excess of 99% and other new useful products are obtained when care is taken to ensure a high partial pressure of chlorine and sufficient mixing and quick dispersion of the 3,5-lutidine or 3,5-lutidine hydrochloride into a chlorine rich diluent which does not substantially compete for the available chlorine. This is accomplished by sparging chlorine (in excess of that needed for the reaction) and 3,5-lutidine or 3,5-lutidine hydrochloride at closely spaced locations near the bottom of the reactor containing the polychlorinated pyridine diluent charge. The mixing required to ensure adequate contact between the liquids and gas can be achieved by high gas flow rate sparging, mechanical agitation, or a combination of both. High gas flow rates as described by Braulich, A. J.; Ch. E. Journal, Volume 11, No. 1, pp. 73–79, can achieve mixing of a magnitude almost equivalent to high power input mechanical mixing. Several disadvantages are inherent in the use of high gas flow rates, however. They are:

(a) high entrainment of the reactor liquids to the scrubber column C1 where they are scrubbed with carbon tetrachloride and must be recycled to the reaction system.

(b) a large volume of chlorine gas which must be purified, dried, and recycled.

Another mode of operation to enhance mixing is to combine mechanical agitation with chlorine gas and 3,5-lutidine or 3,5-lutidine hydrochloride sparging to achieve the desired degree of mixing and excess chlorine. High maintenance of mechanical seals and agitators are some of the disadvantages of such a mechanical agitation system.

An increase in reactor back pressure aids in increasing the chlorine concentration in the reaction liquid. The stoichiometric amount of chlorine reacted per pound of 3,5-lutidine fed is greater than 5:1 by weight. Chlorine in excess of the stoichiometric requirement is considered essential to ensure that the 3,5-lutidine or 3,5-lutidine hydrochloride does not form undesirable tars and polymers. Therefore, weight ratios of at least about 7:1 of chlorine to 3,5-lutidine being fed are deemed necessary in practice of the present process.

Care must be taken not to exceed the thermal stability of the diluent system. Diluents such as 6-chloro- or 5,6-dichloro-2-trichloromethyl pyridine can decompose vigorously at temperatures greater than 260° C.

The above-described embodiments are intended to be illustrative, not restrictive. The full scope of the invention is defined by the claims, and any and all equivalents are intended to be embraced therein.

What is claimed is:

1. The process of noncatalytically chlorinating 3,5-lutidine or 3,5-lutidine hydrochloride in liquid phase without substantial formation of intractable nonvolatiles, said process comprising:

(a) establishing in a reactor means a diluent reactor charge which is made up of chlorinated pyridine and/or lutidine compounds, said diluent being essentially nonreactive with chlorine in the sense of forming two moles or less of hydrogen chloride per mole of diluent under the reaction conditions to which the reactants in the reactor means are subjected;

(b) while maintaining the reactor charge in liquid phase and at a temperature of about 150° C. to 240° C., sparging chlorine and 3,5-lutidine or 3,5-lutidine hydrochloride into the reactor charge near the bottom thereof at a chlorine-to-lutidine feed ratio of at least about 7:1 by weight and at a feed rate low enough so that any separation of the reactor charge into a second, lighter phase composed of unchlorinated 3,5-lutidine hydrochloride is minimized and is in any event less than about 10% of the reactor charge by volume, the excess of chlorine being fed to the reactor charge relative to the amount of 3,5-lutidine being fed thereto providing enhanced agitat2ion of the reaction mass and sufficient chlorine to ensure that the chlorine partial pressure in the vapor space over the reaction mass is greater than 50% of the total pressure;

(c) continuing chlorine addition and maintaining such reaction conditions until substantial side-chain and nuclear substitution of chlorine in the 3,5-lutidine or 3,5-lutidine hydrochloride has occurred; and (d) continuing chlorine addition and maintaining the reaction mass in liquid phase and at a temperature of about 190° C. to 280° C. in a finishing reactor until the desired extent of side-chain and nuclear substitution of chlorine in the 3,5-lutidine or 3,5-lutidine hydrochloride has occurred.

2. The process of claim 1, performed in a continuous batch mode and in a series of at least three reactors, with the first two reactors having initial, essentially inert diluent charges as in step (a) of claim 1, with the reaction conditions of step (b) of claim 1 being maintained in a first reactor, with excess chlorine, hydrogen chloride, and entrained products being transferred by vent line and sparger from the first reactor to the second reactor, with overflow liquid products of chlorination being transferred from the first reactor to the second reactor, the volatile hydrochlorides being absorbed and reacted further in the second reactor, and with overflow liquid from the second reactor being transferred to a third finishing reactor into which third reactor chlorine is sparged.

3. The process of claim 2, comprising continuing chlorination in a finishing reactor until the reaction product comprises at least about 20% 5,6-dichloro-3-trichloromethyl pyridine by weight.

4. The process of claim 2, comprising continuing chlorination is a finishing reactor until the reaction product comprises at least about 20% 2,3,5,6-tetrachloropyridine by weight.

5. The process of claim 2, comprising continuing chlorination in a finishing reactor at a temperature of at least about 190° C., for a time to substantially quantitatively convert the 3,5-bis(trichloromethyl)pyridine and the 2-chloro-3,5-bis(trichloromethyl)pyridine present to 5,6-dichloro-3-trichloromethyl pyridine and/or 2,3,5,6-tetrachloro pyridine.

6. The process of claim 5, comprising continuing chlorination of the reaction mass until substantially all 5,6-dichloro-3-trichloromethyl pyridine is converted to 2,3,5,6-tetrachloro pyridine.

7. The process of claim 2, comprising continuing chlorination in a finishing reactor at a temperature of at least about 190° C. for a sufficient time to convert at least most of the 6-chloro-3,5-bis(trichloromethyl)pyridine and 2,6-dichloro-3,5-bis(trichloromethyl)pyridine to 2,5,6-trichloro-3-trichloro pyridine present, and at least most of the 2,5,6-trichloro-3-trichloromethyl pyridine present to 2,3,5,6-tetrachloro pyridine.

8. The process of claim 7, comprising continuing chlorination of the reaction mass until at least most of the 2,5,6-trichloro-3-trichloromethyl pyridine is converted to 2,3,5,6-tetrachloro pyridine.

9. The process of claim 2, comprising delivering the reaction mass overflow from the second reactor alternately to a third reactor and to a fourth reactor, and sparging chlorine into each of the third and fourth reactors alternately to further chlorinate the reaction mass in a batch manner.

10. The process of claim 2, comprising removing from the third reactor the reaction product formed by further chlorination therein, subjecting such reaction product to product purification by vacuum distillation or the like, and returning the purified volatiles to the third reactor or equivalent for further chlorination.

11. The process of claim 2, wherein the average residence time of the reaction mass in each reactor is from about 1 to about 40 hours and the average total cycle time in the reactors is about 10 to about 120 hours.

12. The process of claim 1, wherein the diluent charged to the reactor means is selected from the group consisting of 3-chloro-, 5-chloro-, 6-chloro-, 5,6-dichloro-, 3,5-dichloro-, 3,6-dichloro-, 3,4,5-trichloro- and 3,5,6-trichloro-2-trichloromethyl pyridine, 2-chloro-, 6-chloro-, 2,6-dichloro-3-trichloromethyl pyridine, 3,5-bis(trichloromethyl)pyridine and 2-chloro- and 2,6-dichloro-3,5-bis(trichloromethyl)pyridine, 2,3,6-trichloro-, 2,3,5,6-tetrachloro- and 2,3,4,5,6-pentachloro pyridine, and mixtures thereof.

13. The process of claim 1, wherein the diluent charged to the reactor is made up essentially of the chlorinated pyridine/lutidine products from a previous reaction.

14. The process of claim 1, wherein the reaction product includes substantial amounts of 2-chloro-3,5-bis(trichloromethyl)pyridine, 2,6-dichloro-3,5-bis(trichloromethyl)pyridine, 3,5-bis(trichloromethyl)pyridine, 5,6-dichloro-3-trichloromethyl pyridine, and 2,5,6-trichloro-3-trichloromethyl pyridine, and 2,3,5,6-tetrachloropyridine.

15. The process of claim 1, wherein the reaction product comprises at least about 20% 5,6-dichloro-3-trichloromethyl pyridine, with the volatile content of the reaction mass being at least about 98%.

16. The process of claim 2, comprising sparging the gases vented from the primary reactor to a secondary reactor, sparging gases from the secondary reactor to an absorber containing an absorbent having a melting point of less than about 80° C. and a substantial solubility with carbon tetrachloride, such absorbent being maintained at a temperature of about 140° and functioning to effectively liquify and remove any higher melting point chloropyridines from the gases sparged thereto, passing the gases vented from the absorber to a refluxing scrubber column maintained at a temperature of from about 30° C. to about 100° C., passing liquid overflow from the secondary reactor to finishing reactor means for further chlorination, and sparging gases vented from said further reactor means into the absorbent contained in said absorber.

17. The process according to claim 16, wherein absorbent media contained in said absorber is selected from the group consisting of 6-chloro-, 5,6,-dichloro-, 3,6-dichloro-, 3,5-dichloro-2-trichloromethyl pyridine, and mixtures thereof.

18. The process of claim 16, wherein the temperature of said primary reactor is maintained at a temperature of at least about 150° C., the temperature of such secondary reactor is maintained at a temperature of from about 150° C. to about 180° C., the temperature of said absorber is maintained at about 140° C., and the temperature of said finishing reactor means is maintained at at least about 190° C.

19. The process of claim 18, wherein liquid outflow from said absorber is subject to removal of polychlorinated pyridines from the absorbent, followed by recycling of the absorbent to the said absorber.

20. The process of chlorinating mixtures rich in 3,5-bis(trichloromethyl)pyridine and/or 6-chloro-3,5-bis(trichloromethyl)pyridine in the liquid phase to form 5,6-dichloro-3-trichloromethyl pyridine and/or 2,3,5,6-tetrachloro pyridine therefrom without substantial formation of intractable nonvolatiles, said process comprising:

(a) establishing in a reactor means a mixture rich in 3,5-bis(trichloromethyl)pyridine and/or 6-chloro-3,5-bis(trichloromethyl)pyridine and a diluent reactor charge which is made up of chlorinated pyridine and/or lutidine compounds, said diluent being essentially nonreactive with chlorine in the sense of forming two moles or less of hydrogen chloride per mole of diluent under the reaction conditions to which the reactants in the reactor means are subjected; and (b) while maintaining the reactor charge in liquid phase at a temperature of about 190° C. to 280° C., sparging chlorine into the reactor charge for a time which is sufficient to convert a substantial portion of the 3,5-bis(trichloromethyl)pyridine and/or the 6-chloro-3,5-bis(trichloromethyl)pyridine to 5,6-dichloro-3-trichloromethyl pyridine and/or 2,3,5,6-tetrachloro pyridine.

21. The process of claim 20, comprising continuing chlorination of the reaction mass until substantially all 5,6-dichloro-3-trichloromethyl pyridine is converted to 2,3,5,6-tetrachloro pyridine.

22. The process of chlorinating mixtures rich in 6-chloro-3,5-bis(trichloromethyl)pyridine and/or 2,6-dichloro-3,5-bis(trichloromethyl)pyridine to form 2,5,6-trichloro-3-trichloromethyl pyridine and/or 2,3,5,6-tetrachloropyridine therefrom without substantial formation of intractable nonvolatiles, said process comprising:

(a) establishing in a reactor means a mixture rich in 6-chloro-3,5-bis(trichloromethyl)pyridine and/or 2,6-dichloro-3,5-bis(trichloromethyl)pyridine and a diluent reactor charge which and is made up of chlorinated pyridine and/or lutidine compounds, said diluent being essentially nonreactive with chlorine in the sense of forming two moles or less of hydrogen chloride per mole of diluent under the reaction conditions to which the reactants in the reactor means are subjected; and (b) while maintaining the reactor charge in liquid phase at a temperature of about 190° C. to 280° C., sparging chlorine into the reactor charge for a time which is sufficient to convert a substantial portion of the 6-chloro-3,5-bis(trichloromethyl)pyridine to 2,6-dichloro-3,5-bis(trichloromethyl)pyridine and at least most of the 2,6-dichloro-3,5-bis(trichloromethyl)pyridine to 2,5,6-trichloro-3-trichloromethyl pyridine and/or 2,3,5,6-tetrachloro pyridine.

23. The process of claim 22, comprising continuing chlorination of the reaction mass until at least most of the 2,5,6-trichloro-3-trichloromethyl pyridine is converted to 2,3,5,6-tetrachloro pyridine.

* * * * *